United States Patent
Vanmaele et al.

(10) Patent No.: US 6,783,735 B2
(45) Date of Patent: Aug. 31, 2004

(54) WEB MATERIAL HAVING WELLS FOR COMBINATORIAL APPLICATIONS

(75) Inventors: Luc Vanmaele, Lochristi (BE); Guido Desie, Herent (BE)

(73) Assignee: Agfa-Gevaert, Mortsel (BE)

( * ) Notice: Subject to any disclaimer, the term of this patent is extended or adjusted under 35 U.S.C. 154(b) by 94 days.

(21) Appl. No.: 09/949,359

(22) Filed: Sep. 7, 2001

(65) Prior Publication Data

US 2002/0034616 A1 Mar. 21, 2002

(30) Foreign Application Priority Data

Sep. 15, 2000 (EP) .............................. 00203182
May 23, 2001 (EP) .............................. 01000183

(51) Int. Cl.$^7$ ................................................. B01L 3/00
(52) U.S. Cl. .................. 422/102; 422/66; 436/44; 435/287.3; 435/288.4
(58) Field of Search ............... 435/286.2–286.4, 435/287.2, 287.3, 287.9, 288.4, 287.8, 305.2, 809; 422/102, 104, 66; 359/398; 356/246; 436/44

(56) References Cited

U.S. PATENT DOCUMENTS

| | | | | |
|---|---|---|---|---|
| 3,615,437 A | * | 10/1971 | Richardson et al. | 430/16 |
| 3,676,080 A | * | 7/1972 | Richterich | 422/66 |
| 4,071,315 A | * | 1/1978 | Chateau | 436/518 |
| 4,349,510 A | * | 9/1982 | Kolehmainen et al. | 422/66 |
| 4,883,642 A | * | 11/1989 | Bisconte | 422/66 |
| 5,077,010 A | * | 12/1991 | Ishizaka et al. | 422/56 |
| 5,210,021 A | * | 5/1993 | Goodwin, Jr. | 435/29 |
| 5,216,925 A | * | 6/1993 | Odernheimer | 73/863.12 |
| 5,605,838 A | * | 2/1997 | Backhaus et al. | 436/34 |
| 5,948,591 A | * | 9/1999 | Vermeersch et al. | 430/270.1 |
| 5,958,345 A | * | 9/1999 | Turner et al. | 422/104 |
| 6,020,026 A | * | 2/2000 | Birch et al. | 427/287 |
| 6,033,740 A | * | 3/2000 | Oelbrandt et al. | 427/511 |

FOREIGN PATENT DOCUMENTS

| | | | | |
|---|---|---|---|---|
| JP | 11064213 A | * | 3/1999 | G01N/21/01 |
| WO | WO 9749987 A1 | * | 12/1997 | G01N/27/02 |
| WO | WO 9845406 A1 | * | 10/1998 | C12N/1/20 |
| WO | WO 9847003 A1 | * | 10/1998 | G01N/33/543 |
| WO | WO 9939829 A1 | * | 8/1999 | B01L/3/00 |

* cited by examiner

Primary Examiner—William H. Beisner
(74) Attorney, Agent, or Firm—Joesph T. Guy; Nexsen Pruet LLC (57) ABSTRACT

A web material is disclosed comprising a substrate in web form and multiple microwells, arranged on the substrate in a predetermined pattern and separated from each other by separating zones, each microwell comprising a bottom and an upstanding surface formed by the adjacent separating zones, wherein the composition of the bottoms on the one hand and the composition of the separating zones and upstanding surfaces on the other hand show a different hyrophilicity.

20 Claims, 2 Drawing Sheets

WEB MATERIAL HAVING WELLS FOR COMBINATORIAL APPLICATIONS

FIELD OF THE INVENTION

The present invention relates to products and methods useful in the field of high troughput screening and combinatorial experimentation.

BACKGROUND OF THE INVENTION

Through the years, chemical and pharmaceutical industry have increasingly relied on High Throughput Screening (HTS) of libraries of chemical compounds, biologically active compounds and cells to identify novel materials or compounds with useful properties. HTS describes a method where many discrete compounds are tested in parallel so that large numbers of test compounds are screened for the useful properties. In recent years combinatorial chemistry methodologies have been increasingly applied to the field of materials science, including homogeneous and heterogeneous catalysis, phosphors for luminescent materials, etc. A review has been presented by Jandeleit et al., Angew. Chem. Int. Ed., 1999, 38, 2494–2532. Many references to material design by combinatorial techniques can be found in this review. Combinatorial search for advanced luminescence materials has also been described in Biotech. & Bioeng., (Combinatorial Chemistry), vol. 61, no. 4, pp. 193–201. Combinatorial techniques for developing new materials have also been extensively used in the patent literature: e.g. U.S. Pat. No. 5,985,356, U.S. Pat. No. 6,004,617, U.S. Pat. No. 6,030,917, U.S. Pat. No. 6,043,363, U.S. Pat. No. 6,045,671 and U.S. Pat. No. 6,034,775.

Currently, the most widely established techniques utilise 96-microwell microtiter plates as a substrate for performing the reactions and/or the testing. In this format, 96 independent tests are performed simultaneously on a single 8 cm×12 cm plastic plate that contains 96 reaction microwells. These microwells typically require assay volumes that range from e.g. 2 to 500 µl. Also microtiter plates with microwells up to 10 or more ml are commercially available.

A problem that arises with such microtiter plates lays in the fact that the construction is truly three dimensional and that the plates occupy, upon storing, quite a large volume. Another problem deals with the microtiter plate handling which requires robots to take the plates out of an input stack, manipulate them for testing, and place them back on a second output stack. Very expensive and complex robots are normally required for this task. True three dimensional movement is necessary and is mostly realised by a rotating arm with extension possibilities and a height control. So rather complex rotational movements must be programmed to come to the required XY-coordinates to handle and analyse the microtiter plates.

The first problem, the required large volume upon storing, can be dealt with by making thinner web materials with a corresponding smaller required stock volume. In WO-A 98/45406 a polymeric substrate is described which is deformed by mechanical pressing so that microvolumes are obtained which can contain the components to be reacted/tested. An additional treatment is required to end up with appropriate hydrophilic/hydrophobic properties. At the end a plate is obtained having thinner substrates and smaller stock volumes after stacking several plates on top of each other.

The second problem, however, remains unsolved, and in most cases the manipulation of thinner plates even becomes much more difficult. Very complex and expensive robots remain required in order to manipulate said discrete web materials.

So there is still a big need to have materials for high throughput screening methodologies which can be handled in a much faster and easier way than conventional plate robots can do.

OBJECTS OF THE INVENTION

It is an object of the invention to provide a web material for combinatorial experimentation that is substantially thin and flexible and that has distinct regions that can accommodate fluids and/or solids.

It is a further object of the invention to provide a flexible web material for high speed screening methodologies, that can be incorporated into a simple workflow and apparatus.

It is still a further object of the invention to provide an apparatus for use with such web material, and a method for using such an apparatus for high throughput screening.

Further objects of the invention will become clear from the detailed description hereinafter.

SUMMARY OF THE INVENTION

The first object of the present invention is realised by providing a web material for combinatorial experimentation comprising a substrate in web form and multiple microwells, arranged on said substrate in a predetermined pattern and separated from each other by separating zones, each microwell comprising a bottom and an upstanding surface formed by the adjacent separating zones, wherein the composition of said bottoms on the one hand and the composition of said separating zones and upstanding surfaces on the other hand show a different hydrophilicity.

The further object of the invention is realised by providing a simple roll-to-roll device wherein a web material for combinatorial experimentation as defined above is used, the device comprising an unwinding section, a component delivery section, a screening section, and optionally a rewinding section.

The invention further encompasses methods for manufacturing web materials as defined above.

DETAILED DESCRIPTION OF THE INVENTION

Figure 1:
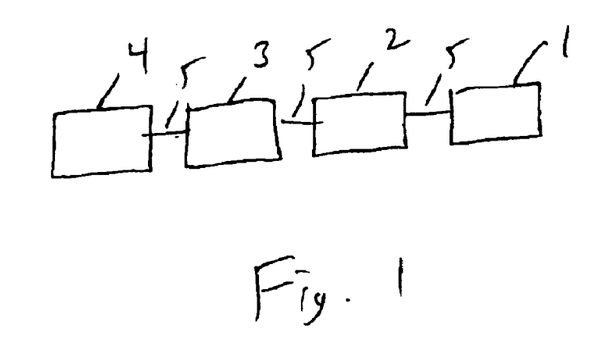
FIG. 1 illustrates an embodiment of the present invention wherein 1 is an unwind, 2 is an application zone, 3 is a screening zone, 4 is a rewind section and 5 is a web.
Figure 2:
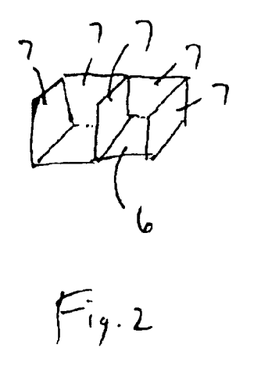
FIG. 2 illustrates an embodiment of the present invention illustrating two microwells, wherein 6 is a bottom and 7 is an upstanding surface.

It was found that it is possible to create on a substrate in web form microwells by introducing according to a predetermined pattern differences in hydrophilicity on multiple regions of said substrate. More particularly a difference in hydrophilicity is created, as will be explained furtheron, between the bottom of each microwell on the one hand and the separating zones and upstanding surface formed by the adjacent separating zones on the other hand. This upstanding surface can also be described as the "wall" of each microwell. This difference in hydrophilicity can be measured by determining the difference in contact angle with a droplet of water between the bottoms on the one hand, and the separating zones and walls on the other hand. It showed that for the purpose of this invention a difference of at least 5° in contact angle when measured with water is appropriate. Preferably said difference in contact angle is of at least 10°. Most preferably the difference in contact angle is at least 25°.

In a first embodiment of this invention, web materials are produced so as to have microwells with a hydrophilic bottom separated by a hydrophobic separating zone and upstanding surface. So in such a web material the contact angle of water with the bottom of the microwells is smaller than the contact angle of water with the separating zone and upstanding surface. Web materials according to this embodiment of the invention are thus very well suited for receiving reagents, solutions, biological fluids, cells, etc. in an aqueous medium in their microwells. Aqueous medium means water, mixtures of water and water miscible solvents such as C1 to C4 alcohols (methanol, ethanol, n-propanol, isopropanol, butanol and mixtures thereof), ketones (acetone, 2-butanone), esters, amides; in fact it means any solvent mixture containing at least 10% of water.

In a second embodiment of this invention, web materials are produced so as to have microwells with a hydrophobic bottom separated from each other by hydrophilic separating zones and upstanding surfaces. Thus in such a web material the contact angle of water with the bottom of the microwells is larger than the contact angle of water with the separating zone and upstanding surface. Web materials according to this embodiment of the invention are thus very well suited for receiving reagents in a an organic non-water miscible solvent.

It was found that in these materials having microwells for combinatorial applications with differences in hydrophilicity the actual volume of liquid that could be introduced into a single microwell was much larger than the theoretical volume. It was even found that a volume of liquid up to 50 times the theoretical volume of the microwell could be accommodated in the microwell and that, even when the microwells were filled up to 50 times their actual volume, the liquid contained in the microwells could be kept into the individual microwell positions without mixing or spoiling, even after placing the web material on a vibration table. Thus the web materials according to this invention can be made thinner than conventional microtiter plates because the microwells can hold a volume that is larger than the physical volume of the microwell. It was also observed that, when a microwell was filled with a solution of a dyestuff in a solvent up to 30 times the actual volume, then the solvent could be evaporated while the dyestuff remained homogenously distributed within the boundaries of the microwell.

The fact that the microwells in web materials of this invention can hold a higher volume of liquid than the actual volume of the microwell makes the web materials of this invention very well suited for reactions between a liquid (a pure liquid or a solution) and a gas, because the liquid extends for a large portion above the surface of the web material; the extending portion presents thus a large reaction surface for the gas that can easily wash around that extending portion.

In a preferred embodiment of the present invention the walls of the microwells are at most 500 μm high, preferably at most 250 μm. Depending on the use, the web materials of this invention can have microwells with walls as low as 0.1 μm.

In web materials according to the invention the bottoms of the microwells can optionally be treated to improve the dynamics of spreading. A surface treatment of the bottom layer can be done to obtain this required effect, or an additional coating can be applied on top of the base material. In both cases the layer thickness of the top surface of the bottom of the microwells is preferably at least 1 μm thick, more preferably at least 5 μm, and most preferably, especially in the case of absorptive coatings, at least 10 μm thick. The spreading can be further improved by increasing the surface roughness of the bottom of the microwells. Expressed in terms of $R_a$ the roughness value is at least 0.25 μm, preferably at least 0.50 μm and even more preferably at least 0.85 μm. Physicochemical techniques such as plasma etching are very well suitable to obtain better spreading characteristics. It is often observed that both the hydrophobic characteristics of the separating zones and the hydrophilic characteristics of the bottom of the microwells are improved after plasma treatment: i.e. both the hydrophilicity of the bottom and the hydrophobicity of the separating zones are improved. Instead of an overall plasma treatment, it is also possible to use a mask in register with the microwells so that only the hydrophilic bottoms, or the hydrophobic separating zones, are treated. In the case of flexible metal plates such as aluminium electrochemical treatments can be used to improve the spreading characteristics. Part of the aluminium can be oxidized to obtain a thicker and more hydrophilic aluminium oxide layer, resulting in improved spreading characteristics. Also for organic polymeric materials, chemical deformation of the bottoms is possible to increase the spreading characteristics: corona treatment, selective oxidation, and specific chemical reactions can be used to alter the spreading characteristics of the bottoms of the microwells. As stated above, it is also possible to apply a separate extra coating composition to the bottom of the microwells, resulting in an additional layer with a thickness of at least 1 μm forming the surface of the bottom of the microwell. Here, coating compositons comprising binders, pigments, and spreading improvement ingredients such as surfactants, oligomers, etc. can be used. For the purpose of easy and cheap fabrication processes this coating composition can be applied to the full area of the substrate prior to applying the hydrophobic composition necessary to form the separating zones and walls of the microwells. After exposure and development, a web material for combinatorial applications is obtained having an absorptive coating on top of the substrate, said coating forming the bottom of the microwell, and being present under the hydrophobic top layer forming the separating zones.

Web materials of this invention can have microwells having any shape, the microwells can be circular, elliptical, oval, square, rectangular, etc. The microwell pattern can also have any geometrical form, but preferably it is a rectangular grid.

Web materials according to this invention can be made so as to have larger microwells, e.g. with diameter at the bottom of 1 cm and an height of 100 μm, of which the bottom is further divided by walls—having a hydrophilicity different from the hydrophilicity of the bottom—in at least two "baby microwells". The walls dividing the bottom of the larger microwell have a height at least 50% lower than the height of the larger microwell. Preferably the height of the walls in the "baby microwells" is at least 75% lower than the height of the larger microwell. The difference in hydrophilicity between the bottom of the larger microwell and the walls dividing the bottom can be chosen smaller than the difference in hydrophilicity between the bottom of the larger microwell and the upstanding surface separating the larger microwells. When screening chemical reactions in, e.g., a web material having 96 larger microwells, the reactants are mixed in the microwells and there is a risk that the reaction starts in microwell 1 at an earlier time than is in microwell 96 due to the time needed to fill the different microwells. With a web material having larger microwells divided in at least two "baby microwells", separated by fairly low walls, the reactants can be brought separately in separate "baby microwells" in each of the 96 larger microwells, and only when all reactants are in place the mixing of the reactants in the 96 larger microwells can proceed simultaneously. This means that the height of the walls and the difference in hydrophilicity of the bottom of the larger microwell and the walls dividing that bottom are chosen so that upon vibration the liquids contained in the "baby microwells" spill over the walls of the "baby microwells" but not over the walls of the larger microwells.

The substrate of the web materials of this invention can be made thin. It can have a thickness between 50 and 1000 $\mu$m, preferably between 50 and 500 $\mu$m. If very thin supports are used in this concept of web material having microwells for combinatorial applications then a very large amount of microwells is available into a single roll of material. If e.g. 50 $\mu$m thick PET is used as substrate, and a 20 $\mu$m thick hydrophilic coating is applied to it combined with a 5 $\mu$m thick hydrophobic masking layer, then a 21 cm wide roll with a diameter of 20 cm on a core of 2 cm diameter can contain more than 750 000 microwells of a typical standard 96-microwell-layout in a single roll, or even more than 12 000 000 microwells in a 1536-microwell-layout!

Web materials having microwells according to this invention have enormous advantages in use if compared with classical microtiter plates. Instead of having to use an expensive and complex robot being able to handle said microtiter plates in a three-dimensional apparatus design, we can use a very simple roll-to-roll design where the microwells are brought to the active zone in the screening process via a very simple unwinding operation. A fixed plate/rotating sleeve can e.g. be mounted in the center of the "screening zone" while without any control and feedback for the height and Y-position the web carrying microwells is transported over said plate and only the X-movement is controlled and adjusted for very accurate localisation of the microwells in the "screening zone". Sampling and analysis can take place by movement over the width of the web or by using a parallel set of sampling/analysis probes. In fact the complexity of the required apparatus can thus be reduced by about 67% compared to traditional microtiter robots. Only the X movement is very important, the rest is "self-adjusting".

The microwells of the web materials of this invention can be coupled to means for heating the content of the microwells, e.g., thermal heating or optical heating and/or to means for stirring the contents of the microwell, e.g., ultrasonic vibrations, piezo-vibrations, etc. Optical techniques and RF-techniques are preferred embodiments for use in said web materials.

The scope of the present invention also encompasses methods for manufacturing web materials as described.

We will now explain in detail the first embodiment of the methods of the invention: manufacturing of web materials having microwells with a hydrophilic bottom separated by a hydrophobic separating zone and upstanding surface.

Web materials having microwells with a hydrophilic bottom separated by a hydrophobic separating zone and upstanding surface can be produced by applying a continuous hydrophobic layer onto a hydrophilic substrate and then pattern-wise removing the hydrophobic layer so as to give rise to microwells with a hydrophilic bottom.

Such web materials can also be prepared by pattern-wise applying the hydrophobic separating zone and upstanding surface on the hydrophilic substrate.

The invention thus encompasses a method for producing a web material, comprising the steps of, in order:
providing a substrate in web form with a homogeneous hydrophilic surface covered with a heat or light sensitive hydrophobic layer having a particular degree of solubility in a developer,
exposing said hydrophobic layer with heat or light to pattern-wise All change said solubility to more or less soluble in said developer, is and
pattern-wise removing by the developer the soluble parts of said exposed hydrophobic heat or light sensitive layer, thereby forming a pattern of multiple microwells with hydrophilic bottoms and hydrophobic upstanding surfaces separated from each other by hydrophobic separating zones.

The invention thus also encompasses a method for producing a web material, comprising the steps of:
providing a substrate in web form with a hydrophilic surface,
pattern-wise applying, preferably by non-impact printing devices, hydrophobic areas on said substrate, thereby forming a pattern of multiple microwells with hydrophilic bottoms and hydrophobic upstanding surfaces separated from each other by hydrophobic separating zones.

The substrate with a hydrophilic surface used for the production of web materials according to this invention can be any hydrophilic substrate. Hydrophilic substrates are very well known in the art of lithographic printing plates. It can be a flexible metal layer, e.g. copper, aluminium, iron, etc, or a metal oxide or a metal that is partly oxidized at its surface; so when a metallic hydrophilic substrate is used, anodized and grained aluminium is a preferred substrate. Also a polymeric sheet or web material containing a metal or metal oxide surface can be used as the hydrophilic substrate, e.g. a polyimide sheet or web whereon a copper layer is present. The hydrophilic substrate can also be any polymeric substrate with a top coating of metals or metal oxides applied to it via chemical or physical vapour deposition or sputtering processes. The substrate material can also be any hydrophilic woven textile, and every textile comprising hydrophobic fibers that have been surface-treated with hydrophilic coatings.

The substrate with the hydrophilic surface can also be a polymer sheet having a hydrophilic surface, e.g. polyesters comprising a large amount, up to 20 to 30%, of moieties carrying sulfonic acid groups. The hydrophilic substrate can also be a polymeric or glass sheet carrying a hydrophilic layer, e.g. a hydrophilic colloid containing layer wherein the hydrophilic colloid can be gelatine, polyvinylalcohol, etc., or a hydrophilic layer containing hydrophilic alumina, silica or titania particles. In the case a hydrophilic layer containing a hydrophilic colloid is used, the layer is preferably hardened, e.g., polyvinylalcohol hardened with TMOS (tetramethylorthosilicate) or with boric acid, or gelatine hardened with formaldehyde.

As explained already earlier the hydrophilic layer can be a rather thick liquid absorbing layer, e.g. a boehmite layer. The thickness of said absorbing hydrophilic layer is preferably larger than 10 $\mu$m, even in the range of 30 to 100 $\mu$m, so that a very large amount of dispensed liquid can be captured. As well known to those skilled in the art of photographic film fabrication, the physical characteristics of said absorbing bottom layer can be made to be very anisotropic, e.g. by sol-gel drying, so that lateral diffusion under the separating surface is even more restricted. If lateral diffusion of a component is not wanted or has to be prevented, an absorbing, hydrophilic coating can be applied in each finished microwell separately instead of a continuous absorbing coating, each microwell having a non-absorbing surface.

On top of such a hydrophilic layer a continuous hydrophobic layer is applied. The hydrophobic layer can be a photosensitive or heat sensitive layer. The hydrophobic layer comprises preferably an alkali soluble polymer, or a combination of a such a polymer with a so-called insolubiliser, also called inhibitor. The solubility of this polymer, or of the polymer-inhibitor complex in a developer, i.e. in most instances the solubility in an alkaline solution, is capable of being differentiated upon exposure by heat or light, i.e. the solubility of the polymer is decreased (negative working), or the solubility of the polymer-complex is increased (positive working) by disruption of the complex. Both negative and positive working layers can be used to produce a web material according to this invention. Very useful light or heat sensitive hydrophobic layers are those that have been disclosed in connection with the production of lithographic printing plates. For sake of this invention the formulation of the layers and the thickness of the coatings thereof has to be adapted.

An overview of hydrophobic layers that are heat sensitive and that are useful in the fabrication of web materials according to this invention, has been given by R. Goodman and B. Nussel in TAGA 99 pages 264–279 in an article titled: The Technology Generations of Digital Thermal Printing Plates presented at the 99 conference of the Technical Association of Graphic Arts (TAGA) held April 1999 and published in the Proceedings of this conference. Useful heat sensitive layers can be layers containing a phenolic resin, a cross-linker, a thermal acid generator and an IR absorbing dye or pigment as disclosed in, e.g., EP-A-819 980, EP-A-819 985, EP-A-795 789, U.S. Pat. No. 5,491,046, U.S. Pat. No. 5,466,557, U.S. Pat. No. 5,340,699, U.S. Pat. No. 5,663,037, U.S. Pat. No. 5,814,431, etc. In such layers upon heating the phenolic resin is cross-linked and thus insolubilised at the exposed areas.

Other useful thermosensitive layers for use in the production of web materials according to this invention are layers containing a phenolic resin and a insolubiliser/inhibitor; this inhibitor forms hydrogen bonds with the phenolic resin and makes it insoluble in the developer. After heat exposure, the hydrogen bonds are broken in the exposed areas and the resin becomes soluble. Such layers have been disclosed in, e.g., WO-A-98/54621, WO-A-98/42507, U.S. Pat. No. 5,858,626, EP-A-823 327, EP-A-825 927, etc. Further useful heat sensitive hydrophobic layers for use in the production of web materials according to this invention are layers containing a dispersion of hydrophobic thermoplastic (heat softenable core/aqueous soluble shell) polymer particles in a hydrophilic binder which coalesce under IR laser exposure to form the insoluble image areas. Such layers have been disclosed in, e.g., EP-A-514 145, EP-A-599 510, WO-A-98/51496, EP-A-773 112, WO-A-98/53994, etc. Also heat sensitive hydrophobic layers as disclosed in EP-A-864 420 and EP-A-881 094.

Ablative layers, wherein the hydrophobic layer is imagewise ablated by IR-exposures, can be used for the production of web materials according to the invention. Such layers have been disclosed in, e.g., EP-A-628,409, WO-A-98/55330, U.S. Pat. No. 5,401,611, DE-A-19748711, U.S. Pat. No. 5,605,780, U.S. Pat. No. 5,691,114, WO-A-97/00735, U.S. Pat. No. 4,054,094, EP-A-882 582, etc.

Light sensitive hydrophobic layers for use in the production of web materials can also be positive or negative working. A positive working light sensitive hydrophobic layer is usually based on the diazoquinone/novolak system, also used in photoresists for the electronics industry. Typical photoresists useful for making the hydrophobic layer are sold by SHIPLEY Company, L.L.C. Marlborough, Mass., USA. The diazoquinone can be, e.g., a compound as the ones described in J. Kosar, Light-Sensitive Systems, pp. 339–352, John Wiley & Sons Inc., o-quinonediazide sulfonic acid esters or o-quinonediazide sulfonic acid amides obtained by the reaction with various kinds of aromatic polyhydroxy compounds or aromatic amino compounds ester of benzoquinone-(1,2)-diazidosulfonic acid chloride or naphthoquinone-(1,2)-diazido-5-sulfonic acid chloride and a pyrogallol-acetone resin, as disclosed, e.g., in JP-B-43-28403, and the ester of benzoquinone-(1,2)-diazidosulfonic acid chloride or naphthoquinone-(1,2)-diazido-5-sulfonic acid chloride and a phenol-formaldehyde resin, as disclosed, e.g., in U.S. Pat. Nos. 3,046,120 and 3,188,210. Further, the ester of naphthoquinone-(1,2)-diazido-4-sulfonic acid chloride and a phenol-formaldehyde resin or a cresol-formaldehyde resin, and the ester of naphthoquinone-(1,2) diazido-4-sulfonic acid chloride and a pyrogallol-acetone resin. The resins with polyhydric groups forming the ester with the benzoquinone-(1,2)-diazidosulfonic acid or with the naphthoquinone-(1,2)-diazido sulfonic acid are preferably low molecular weight resins.

Typical useful novolak resins are, e.g., a phenol-formaldehyde resin, a m-cresol-formaldehyde resin, p-cresol-formaldehyde resin, an o-cresol-formaldehyde resin, a m-cresol/p-cresol mixture-formaldehyde resin and phenol/cresol mixture-formaldehyde resins (wherein the cresol may be m-cresol, p-cresol, o-cresol or a m-cresol/p-cresol mixture, a m-cresol/o-cresol mixture or a o-cresol/p-cresol mixture). Other phenol resins of resol type are also suitable for use in the hydrophobic layer, e.g., phenol/cresol mixture-formaldehyde resins (wherein the cresol may be m-cresol, p-cresol, o-cresol or a m-cresol/p-cresol mixture, a m-cresol/o-cresol mixture or a o-cresol/p-cresol mixture).

A negative working light sensitive hydrophobic layer preferably comprises a diazonium salt, a diazonium resin or an aryldiazosulfonate homo- or copolymer. Examples of low-molecular weight diazonium salts for use in the present invention include: benzidine tetrazoniumchloride, 3,3'-dimethylbenzidine tetrazoniumchloride, 3,3'-dimethoxybenzidine tetrazoniumchloride, 4,4'-diaminodiphenylamine tetrazoniumchloride, 3,3'-diethylbenzidine tetrazoniumsulfate, 4-aminodiphenylamine diazoniumsulfate, 4-aminodiphenylamine diazoniumchloride, 4-piperidino aniline diazoniumsulfate, 4-diethylamino aniline diazoniumsulfate and oligomeric condensation products of diazodiphenylamine and formaldehyde. Said layer preferably comprises a positive or negative working photoresist as active ingredient, i.e. a compound or composition of which the solubility can be differentiated upon exposure. Upon exposure the diazo resins or diazonium salts are converted from water soluble to water insoluble (due to the destruction of the diazonium groups) and additionally the photolysis products of the diazo may increase the level of cross-linking of the polymeric binder or diazo resin, thereby selectively converting the surface, in an image-wise pattern, from water-soluble to water-insoluble. The unexposed areas remain unchanged, i.e. water-soluble. An overview of both negative and positive working layers and ingredients contained in them have been disclosed in European patent application, appl. No. 00202216 filed on Jun. 26, 2000.

When web materials comprising multiple microwells according to this invention are produced by providing a substrate with a hydrophilic surface and pattern-wise applying a hydrophobic pattern on said substrate, then it is preferred to apply the hydrophobic pattern by contact printing (e.g. rotary screen printing) or non-impact printing, especially by ink-jet printing. The methods for imagewise applying solutions to a hydrophilic substrate as known from the art of lithographic printing plate preparation can be used for preparing web materials of this invention. Hydrophobic solutions that can be applied by ink-jet to a hydrophilic substrate are well known and have been disclosed, e.g., in WO-A-94/11191, in JP-A-62-25081, wherein it is disclosed to apply an ink, containing titanate or silane coupling agents by ink jet printing onto a hydrophilic surface, in U.S. Pat. No. 4,833,486 wherein it is disclosed to deposit a hot wax on a hydrophilic surface. Also in JP-A-1-13456 methods for applying, e.g. curable silicones on a hydrophilic substrate are disclosed. Also the methods disclosed in U.S. Pat. No. 5,511,477 and U.S. Pat. No. 5,312,654 can be used for the production of web materials of this invention.

We will now explain in detail the second embodiment of the methods of this invention: the manufacturing of a web material having microwells with a hydrophobic bottom separated from each other by a hydrophilic separating zone and upstanding surface.

Such web materials are well suited for reactions in organic non-aqueous solvents or in oleophilic solvents.

Web materials according to this second embodiment can be made starting from a heat sensitive material having, in order, a support, a hydrophobic layer and a hydrophilic layer. Basically such material is patterned with multiple microwells as follows: upon pattern-wise exposure with heat, e.g., with a IR-emitting laser, the overlaying hydrophilic layer is ablated, thus producing microwells with a hydrophobic bottom and hydrophilic upstanding surface separated from each other by hydrophilic separating zones.

Thus the invention encompasses also a method for producing web materials having microwells with a hydrophobic bottom separated by a hydrophilic separating zone and upstanding surface, comprising the steps of imagewise ablating the hydrophilic top layer to free the hydrophobic bottom of the resulting microwell.

The hydrophobic layer can be the substrate of the web material itself, e.g. a polymer as polyethylene terephthalate, polyethylene naphthalate, polyethylene, polypropylene, polystyrene, etc. or it can be a layer coated on a support. When the layer is coated on said support is contains preferably a binder and a substance capable of converting light into heat. This latter substance can be selected from the group consisting of carbon black, infrared or near infrared absorbing dyes or pigments, metals such as Bi, Sn, Te etc. or a combination thereof. The hydrophobic binder is preferably selected from the group consisting of cellulose esters, cellulose nitrate, a copolymer of vinylidene chloride and acrylonitrile, poly(meth)acrylates, polyvinyl chloride, and polycarbonates. From these polymers, a polymer containing nitrate ester groups, a polymer containing carbonate groups and a polymer containing covalently bound chlorine are preferred.

The hydrophilic layer contains hydrophilic binders having free reactive groups including e.g. hydroxyl, carboxyl, hydroxyethyl, hydroxy-propyl, amino, aminoethyl, aminopropyl, carboxymethyl, etc., along with suitable cross-linking or modifying agents including e.g. hydrophilic organotitanium reagents, aluminoformyl acetate, dimethylol urea, melamines, aldehydes, hydrolyzed tetraalkyl orthosilicate, etc. Such polymers are selected from the group consisting of gum arabic, casein, gelatin, starch derivatives, carboxymethyl cellulose and Na salt thereof, cellulose acetate, sodium alginate, vinyl acetate-maleic acid copolymers, styrenemaleic acid copolymers, polyacrylic acids and salts thereof, polymethacrylic acids and salts thereof, hydroxy-ethylene polymers, polyethylene glycols, hydroxypropylene polymers, polyvinyl alcohols, and hydrolyzed polyvinylacetate having a hydrolyzation degree of at least 60% by weight and more preferably at least 80% by weight.

Web materials according to this invention can be made double sided, i.e. the substrate can carry microwells on both sides of it. When made double sided, the web materials can carry on both sides a web material prepared according to the first embodiment of the invention, or on both sides a web material prepared according to the second embodiment of the invention, or on one side a web material prepared according to the first embodiment of the invention and on the other side a web material prepared according to the second embodiment.

Web materials having microwells for combinatorial applications according to this invention preferably have an aspect ratio (length over width) of more than 5, more preferably an aspect ratio of more than 20, and even most preferably an aspect ratio of more than 100. Web materials having microwells for combinatorial applications according to this invention showing a large aspect ratio preferably comprise more than 1000 microwells per roll, more preferably even more than 100 000 microwells per roll. Web materials with a thin substrate and a rather small width can be used in simple roll-to-roll devices where linear substrate movement is done with a simple rotation of the roll, while scanning over the width of the web can be done using a shuttle mechanism, as e.g. known in the art of ink jet printing, or an array of application and/or screening tools can be placed in a rigid configuration orthogonal to the substrate movement.

When using said web materials having microwells for combinatorial applications for high throughput screening purposes, it is advantageous to include a marking system onto the web material. During the fabrication of the web material having microwells for combinatorial applications, it is e.g. possible to include a barcode at different locations, so that addressing of a long web with an enormous amount of microwells can be done quite easily and fast. The additional information can also be applied to the beginning and/or to the end of the web material. It can be applied to said web by impact technologies such as label stickers, thermal transfer printing, screen printing, flexo printing, gravure printing, offset printing. It can also be applied by non-impact printing technologies such as ink jet printing, toner jet printing, direct laser marking, etc . . . .

The web material having microwells for combinatorial applications according to the present invention can be used for a wide variety of applications. It can be used in reflection or transparency mode with hydrophilic transparent microwells into which components are applied that have to be screened using spectroscopic or densitometric techniques. The web material as described above can have wells of which the hydrophobic zones including the walls have a specific colour to prevent for example cross-talk between adjacent wells during spectroscopic evaluation. An anodised aluminium web treated with hydrophobic photopolymeric microwell-walls can be used to dispense reaction components after which the reaction product (optionally after a higher temperature treatment) can be screened for properties such as IR-absorption, luminescent emission, e.g. phosphorescence, gloss characteristics, or any relevant characteristic that is related to the resultant finalized product.

The web material as described above can be used to contain human or animal cell cultures, bacteria, viruses, genetically modified cells, etc. and their additives to the microwell locations that can be stored on roll and analysed later on (e.g. after 24 hours, or after 7 days) for cell growth.

The scope of the present invention further encompasses an apparatus for rapid screening of substances for useful applications comprising:
- a holder, comprising an unwinding roll, for a web material having microwells for combinatorial experimentation according to the invention,
- an application zone suited for applying at least one substance in at least one of said microwells present in said application zone,
- a screening zone for determining a useful property of said substance in said screening zone, and
- a mechanism to transport said web material from said holder to said application zone and said screening zone,
- optionally a rewinding section.

The scope of the present invention further encompasses a method of rapid screening of substances for useful properties comprising the steps of, in order:
- unrolling a web material as explained above from an unwinding roll present in the holder of an apparatus as defined above,
- passing said web material through the application zone of said apparatus to apply at least one substance in at least one of said microwells present in said application zone,
- passing said web material through the screening zone of said apparatus for determining a useful property of said at least one substance,
- optionally rewinding said web material.

For instance, the web material can be used in a roll-to-roll process comprising the steps of dispensing a growth medium, an active biological material, an activity blocker and/or activity enhancer, an additive to visualise the effect of some activity (e.g. a colour test reagent), a fixing agent to stabilize the shown activity after a certain period of time, and a screening step in which e.g. spectroscopic techniques are used to measure and store the resultant activity data in a database.

In order to prevent well contamination caused by lateral diffusion of biological material through the uniformally applied absorbing hydrophilic coating, the growth medium can also be applied separately into each well having a non-absorbing surface during the fabrication of the microwell plates.

The web material can be combined in a roll-to-roll process with a second web material having interleave properties. So both the web material comprising the microwells and a second interleave material having no microwells can be unwound, the microwells can be filled and analysed for useful properties, and then the web material having the filled microwells can be wound with an interleave material of the other web on top of the microwells. In this way cross-contamination between different microwells making contact during winding can be prevented. The interleave web material can be transparent, translucent, black, moisture impermeable, etc. It can even have adhesive strips so that e.g. at the edges a good contact is made with the web material comprising filled microwells. It must be clear for those skilled in the art that any other method to prevent cross-contamination between separate microwells, e.g. including beads into the area surrounding the microwells, may be envisaged.

The present invention will now be illustrated by the following examples without however being limited thereto.

EXAMPLES

A 24 cm wide roll of PET substrate was coated with a 20 $\mu$m thick hydrophilic coating comprising 90% of hydrophilic boehmite, 9% of polyvinylalcohol and 1% of boric acid as cross-linker for the binder. On top of this hydrophilic coating a 20 $\mu$m thick layer of photoresist Shipley SU-8, to which 10% (w/w) of carbon black was added to give the photoresist layer and the resulting separating zones a black color, was applied, exposed pattern-wise through a mask to light with a wavelength of 350 nm. After development in a commercial developer (NANO XP SU-8 Developer from MicroChem. Corp.) microwells were formed with a diameter at the bottom of 7 mm. A web material was obtained comprising 1800 wells per meter running length.

For a second example the photoresist was pattern-wise deposited using screenprinting technology (15 $\mu$m) and no development was performed. These materials in web format were used in a roll-to-roll apparatus delivering multiple sets of pigmented ink jet inks comprising 5% of pigment in water/isopropanol mixtures, drying said deposited areas of pigments, and recording the spectral characteristics of each of said deposited pigmented inks by means of a multi-fiber-optic based spectral analysis system. After spectral analysis the complete roll of material was stored for later retrieval or reuse.

The methodology as described in the example enables more flexible and faster screening than the traditional experiments in which true ink jet compositions are prepared, jetted using XY-controlled ink jet printers to conventional substrates and analysed afterwards on an individual basis.

What is claimed is:

1. A web material for combinatorial experimentation comprising a substrate in web form and multiple microwells, arranged on said substrate in a predetermined pattern and separated from each other by separating zones, each microwell comprising a bottom and an upstanding surface formed by the adjacent separating zones, wherein the composition of said bottoms on the one hand and the composition of said separating zones and upstanding surfaces on the other hand show a different hydrophilicity and in which said bottom of each of said microwells is further divided by a wall having a hydrophilicity different from the hydrophilicity of said bottom into at least two "baby microwells", said wall having a height at least 50% lower than the height of said upstanding surface.

2. Web material according to claim 1, wherein said wall has a height at least 75% lower than the height of said upstanding surface.

3. Web material according to claim 1, wherein said upstanding surface extends at most 500 $\mu$m above the bottom of said microwells.

4. Web material according to claim 1, wherein said bottoms of said microwells have undergone a surface treatment to improve the dynamics of fluid spreading.

5. Web material according to claim 1, wherein the total amount of microwells present on said web material is larger than 1000.

6. Web material according to claim 1, wherein the ratio of the total length (L) of said web to its width (W) is greater than 20.

7. Web material according to claim 1, wherein said microwells have an internal volume smaller than 10 μl.

8. Web material according to claim 1, wherein a plurality of markers is present on said web material in the web direction.

9. Web material according to claim 8, wherein said marker is a barcode present at the edge of the substrate.

10. Web material according to claim 1, wherein an identifier is present at the start and/or the end of the web.

11. Web material according to claim 1, wherein said substrate is a flexible polymeric material.

12. Web material according to claim 11, wherein said flexible polymeric material is chosen from polyesters and polyimides.

13. Web material according to claim 1, wherein said substrate is a flexible metal or metal oxide.

14. Web material according to claim 13, wherein said substrate is an aluminium foil having a top layer of aluminium oxide applied by electrochemical oxidation.

15. Web material according to claim 1 wherein said substrate is flexible glass.

16. A method for manufacturing a web material having microwells for combinatorial experimentation comprising a substrate in web form and multiple microwells, arranged on said substrate in a predetermined pattern and separated from each other by separating zones, each microwell comprising a bottom and an upstanding surface formed by the adjacent separating zones, wherein the composition of said bottoms on the one hand and the composition of said separating zones and upstanding surfaces on the other hand show a different hydrophilicity and in which said bottom of each of said microwells is further divided by a wall having a hydrophilicity different from the hydrophilicity of said bottom into at least two "baby microwells", said wall having a height at least 50% lower than the height of said upstanding surface, said method comprising the steps of, in order:

providing a substrate in web form with a homogeneous hydrophilic surface covered with a heat or light sensitive hydrophobic layer having a particular degree of solubility in a developer, exposing pattern-wise said hydrophobic layer with heat or light to pattern-wise change said solubility to more or less soluble in said developer, and pattern-wise removing by said developer the soluble parts of said exposed hydrophobic heat or light sensitive layer, thereby forming a pattern of multiple microwells with hydrophilic bottoms and hydrophobic upstanding surfaces separated from each other by hydrophobic separating zones and in which said bottom of each of said microwells is further divided by a wall having a hydrophilicity different from the hydrophilicity of said bottom into at least two "baby microwells", said wall having a height at least 50% lower than the height of said upstanding surface.

17. A method for manufacturing a web material having microwells for combinatorial experimentation comprising a substrate in web form and multiple microwells, arranged on said substrate in a predetermined pattern and separated from each other by separating zones, each microwell comprising a bottom and an upstanding surface formed by the adjacent separating zones, wherein the composition of said bottoms on the one hand and the composition of said separating zones and upstanding surfaces on the other hand show a different hydrophilicity, said method comprising the steps of, in order:

providing a substrate in web form with a hydrophilic surface, pattern-wise applying hydrophobic areas on said substrate, thereby forming a pattern of multiple microwells with hydrophilic bottoms and hydrophobic upstanding surfaces separated from each other by hydrophobic separating zones and in which said bottom of each of said microwells is further divided by a wall having a hydrophilicity different from the hydrophilicity of said bottom into at least two "baby microwells", said wall having a height at least 50% lower than the height of said upstanding surface.

18. A method for manufacturing a web material having microwells for combinatorial experimentation comprising a substrate in web form and multiple microwells, arranged on said substrate in a predetermined pattern and separated from each other by separating zones, each microwell comprising a bottom and an upstanding surface formed by the adjacent separating zones, wherein the composition of said bottoms on the one hand and the composition of said separating zones and upstanding surfaces on the other hand show a different hydrophilicity and in which said bottom of each of said microwells is further divided by a wall having a hydrophilicity different from the hydrophilicity of said bottom into at least two "baby microwells", said wall having a height at least 50% lower than the height of said upstanding surface, said method comprising the steps of, in order:

providing a substrate in web form with a hydrophobic surface covered with a hydrophilic layer, pattern-wise ablating by heat parts of said hydrophilic layer, thereby forming a pattern of multiple microwells with hydrophobic bottoms and hydrophilic upstanding surfaces separated from each other by hydrophilic separating zones and in which said bottom each of said microwells is further divided by a wall having a hydrophilicity different from the hydrophilicity of said bottom into at least two "baby microwells", said wall having a height at least 50% lower than the height of said upstanding surface.

19. An apparatus for rapid screening of substances for useful applications comprising:

a holder, comprising an unwinding roll, for a web material having microwells for combinatorial experimentation comprising a substrate in web form and multiple microwells, arranged on said substrate in a predetermined pattern and separated from each other by separating zones, each microwell comprising a bottom and an upstanding surface formed by the adjacent separating zones, wherein the composition of said bottoms on the one hard and the composition of said separating zones and upstanding surfaces on the other hand show a different hydrophilicity and in which said bottom of each of said microwells is further divided by a wall having a hydrophilicity different from the hydrophilicity of said bottom into at least two "baby microwells", said wall having a height at least 50% lower than the height of said upstanding surface, an application zone suited for applying at least one substance in at least one of said baby microwells present in said application zone, a screening zone for determining a useful property of said substance in said screening zone, a mechanism to transport said web material from said holder to said application zone and said screening zone, and optionally a rewinding section.

20. A method of rapid screening of substances for useful properties comprising the steps of, in order:

unrolling a web material for combinatorial experimentation comprising a substrate in web form and multiple microwells, arranged on said substrate in a predetermined pattern and separated from each other by separating zones, each microwell comprising a bottom and an upstanding surface formed by the adjacent separating zones, wherein the composition of said bottoms on the one hand and the composition of said separating zones and upstanding surfaces on the other hand show a different hydrophilicity and in which said bottom of each of said microwells is further divided by a wall having a hydrophilicity different from the hydrophilicity of said bottom into at least two "baby microwells", said wall having a height at least 50% lower than the height of said upstanding surface from an unwinding roll present in the holder of an apparatus according to claim 19, passing said web material through the application zone of said apparatus to apply at least one substance in at least one of said baby microwells present in said application zone, passing said web material through the screening zone of said apparatus for determining a useful property of said at least one substance, optionally rewinding said web material.

* * * * *